US007723041B2

(12) United States Patent
Lou et al.

(10) Patent No.: US 7,723,041 B2
(45) Date of Patent: May 25, 2010

(54) ASSAY FOR SARS CORONAVIRUS BY AMPLIFICATION AND DETECTION OF THE REPLICASE SEQUENCE

(75) Inventors: Jianrong Lou, Boyds, MD (US); James A. Price, Jr., Lutherville, MD (US); Daretta A. Yursis, Parkton, MD (US); David M. Wolfe, Red Lion, PA (US); Lisa M. Keller, York, PA (US); Tobin Hellyer, Westminster, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/322,520

(22) Filed: Feb. 3, 2009

(65) Prior Publication Data

US 2009/0258340 A1    Oct. 15, 2009

Related U.S. Application Data

(63) Continuation of application No. 10/570,704, filed as application No. PCT/US2004/029691 on Sep. 13, 2004, now Pat. No. 7,521,185.

(60) Provisional application No. 60/502,279, filed on Sep. 12, 2003.

(51) Int. Cl.
*C12Q 1/68* (2006.01)
(52) U.S. Cl. .......................... 435/6; 435/91.1; 435/91.2; 536/24.33
(58) Field of Classification Search ........................ None
See application file for complete search history.

(56) References Cited

U.S. PATENT DOCUMENTS

| 5,270,184 | A | 12/1993 | Walker et al. |
| 5,455,166 | A | 10/1995 | Walker |
| 5,523,204 | A | 6/1996 | Singer et al. |
| 5,547,861 | A | 8/1996 | Nadeau et al. |
| 5,550,025 | A | 8/1996 | Walker |
| 5,593,867 | A | 1/1997 | Walker et al. |
| 5,648,211 | A | 7/1997 | Fraiser et al. |
| 5,691,145 | A | 11/1997 | Pitner et al. |
| 5,744,311 | A | 4/1998 | Fraiser et al. |
| 5,756,702 | A | 5/1998 | Lohman et al. |
| 5,846,726 | A | 12/1998 | Nadeau et al. |
| 5,888,739 | A | 3/1999 | Pitner et al. |
| 5,916,779 | A | 6/1999 | Pearson et al. |
| 5,928,869 | A | 7/1999 | Nadeau et al. |
| 5,935,791 | A | 8/1999 | Nadeau et al. |
| 6,316,200 | B1 | 11/2001 | Nadeau et al. |
| 6,656,680 | B2 | 12/2003 | Nadeau et al. |
| 6,743,582 | B2 | 6/2004 | Nadeau et al. |
| 2005/0233314 | A1 | 10/2005 | Juang et al. |

FOREIGN PATENT DOCUMENTS

| CN | 1483737 | 3/2004 |
| CN | 1488646 | 4/2004 |
| EP | 0657548 | 6/1995 |
| EP | 0878553 | 11/1998 |

OTHER PUBLICATIONS

CDC Guidelines and Recommendations: Guidelines for Laboratory Diagnosis of SARS-CoV Infection, Jan. 8, 2004. cited by other.
Drosten et al., "Identification of a Novel Coronavirus in Patients with Severe Acute Respiratory Syndrome," The New England Journal of Medicine, 2003, vol. 348, No. 20, pp. 1967-1976. cited by other.
Rota et al., "Characterization of a Novel Coronavirus Associated with Severe Acute Respiratory Syndrome," Science, 2003 vol. 300, pp. 1394-1399. cited by other.
Walker et al, Strand Displacement Amplification—An Isothermal, in vitro DNA Amplification Technique, Nucleic Acids Research, 1992, vol. 20, No. 7, pp. 1691-1696. cited by other.
Walker et al., "Isothermal in vitro Amplification of DNA by a Restriction Enzyme/DNA Polymerase System," Proc. Natl. Acad. Sci. USA, 1992 vol. 89, pp. 392-396. cited by other.
Nadeau et al., "Real-Time Sequence-Specific Detection of Nucleic Acids during Strand Displacement Amplification," Analytical Biochemistry, 1999, vol. 276, pp. 177-187. cited by other.
Ausubel et al., Current Protocols in Molecular Biology (John Wiley & Sons, 1998), 2.10-2.10.16, 6.3.1-6.3.6. cited by other.
Qin et al., SARS Coronavirus BJ03, NCBI Nucleotide Accession No. AY278490, Apr. 17, 2003, Institute of Microbiology and Epidemiology, Academy of Military Medical Sciences/Beijing Genomics Institute, Chinese Academy of Sciences, Beijing, Beijing101300, China, cited by other.
Pieris et al., Clincial Progression and Viral Load in a Community Outbreak of Coronavirus-associated SARS Pneumonia: A Prospective Study, Lancet, 2003, vol. 361, pp. 1767-1772. cited by other.
Poon et al., "Rapid Diagnosis of a Coronavirus Associated with Severe Acute Respiratory Syndrome (SARS)," Clinical Chemistry, 2003, vol. 49, No. 6, pp. 953-955. cited by other.
Poon et al., Detection of SARS Coronavirus in Patients with Severe Acute Respiratory Syndrome by Conventional and Real-Time Quantitative Reverse Transcription-PCR Assays, Clinical Chemistry, 2004, vol. 50, No. 1, pp. 67-72. cited by other.
Poon et al., "Early Diagnosis of SARS Coronavirus Infection by Real Time RT-PCR," Journal of Clinical Virology, 2003, vol. 28, pp. 233-238. cited by other.

*Primary Examiner*—Heather G. Calamita
(74) *Attorney, Agent, or Firm*—Lerner, David, Littenberg, Krumholz & Mentlik, LLP

(57) ABSTRACT

Primers and probes derived from SARS-CoV nucleic acid that facilitate detection and/or quantification of the replicase gene are disclosed. The disclosed sequences may be used in a variety of amplification and non-amplification formats for detection of SARS-CoV infection.

27 Claims, No Drawings

ASSAY FOR SARS CORONAVIRUS BY AMPLIFICATION AND DETECTION OF THE REPLICASE SEQUENCE

CROSS REFERENCE TO RELATED APPLICATIONS

This application is a continuation of U.S. application Ser. No. 10/570,704 filed Mar. 21, 2007, which is a U.S. National Phase Application of International Application No. PCT/US04/29691, filed Sep. 13, 2004, which claims priority to U.S. Provisional Application No. 60/502,279, filed Sep. 12, 2003, the disclosures of all of which are incorporated by reference herein.

TECHNICAL FIELD

The present invention relates to methods to assay for the presence of Severe Acute Respiratory Syndrome coronavirus by amplification and detection of the replicase RNA sequence.

BACKGROUND ART

Severe acute respiratory syndrome (SARS) is a recently emerging disease associated with atypical pneumonia in infected patients. The disease is unusually severe, and there is no known treatment. The incubation period for. SARS is typically between 2 and 10 days. Sympathkumar et al., *Mayo Clin. Proc.* 78:882-890 (2003). Physical manifestations of SARS include fever, followed by a dry, nonproductive cough and shortness of breath. Death from respiratory failure occurs in about 3% to 10% of SARS cases. Centers for Disease Control and Prevention (CDC). *Morb. Mortal. Wkly. Report.* 52:357 (2003).

Clinical diagnosis of SARS is often a slow process because initial diagnostic testing of suspected SARS patients includes a chest radiograph, pulse oximetry, blood culture, sputum Gram's stain and culture, and testing for other viral respiratory infections. CDC, *Guidelines and Recommendations: Interim Guidelines for Laboratory Diagnosis of SARS-CoV Infection*, July (2003). This difficulty is also reflected by the fact that two of the most common diagnostic procedures—detection of serum antibodies to the SARS virus and isolation in cell culture of the virus from a clinical specimen—often take days or even weeks to complete. CDC, *Guidelines and Recommendations: Interim Guidelines for Laboratory Diagnosis of SARS-CoV Infection*, July (2003). Thus, the need for the establishment of a rapid and noninvasive test for SARS is essential for monitoring and control of the disease.

Early in 2003, a novel coronavirus was identified as the causative agent of SARS. Drosten et al., *N. Engl. J. Med.* 348:1967-76 (2003). The coronaviruses are a diverse group of RNA viruses that cause respiratory and enteric diseases in humans and other animals. They are the largest of the RNA viruses, with a genome of approximately 30,000 nucleotides. Rota et al., *Science* 300:1394-1399 (2003). The SARS-Coronavirus (SARS-CoV) is an enveloped, positive-stranded RNA virus. Based on sequence analysis, SARS-CoV is a member of a new group of coronavirus (order Nidovirales, Family Coronaviridae, genus *Coronavirus*). Rota et al., supra.

The replicase (rep) gene, is located towards the 5' end of the genomic RNA and comprises approximately 70% of the whole genome. In contrast with other viral proteins, the rep gene products are translated from the genomic RNA. The replicase polyprotein undergo autocatalytic cleavage to yield functional viral proteases, RNA polymerase and RNA-dependent helicase. Detection of the rep gene may be used as an indicator of the presence of genomic SARS-CoV RNA. Rota et al., supra. An assay that tests for the presence of the viral nucleic acid would therefore allow for the rapid and sensitive detection of SARS-CoV. Such an assay would provide a more sensitive alternative to serological testing, direct fluorescent antibody staining or urinary antigen testing.

DISCLOSURE OF INVENTION

According to one aspect, the present invention provides an oligonucleotide set comprising a first amplification primer and a second amplification primer, the first amplification primer selected from the group consisting of SEQ ID NOs:2 and 14 and the second amplification primer selected from the group consisting of SEQ ID NOs:3 and 15. In another aspect, the first amplification primer consists essentially of SEQ ID NO:2 and the second amplification primer consists essentially of SEQ ID NO:3. In yet another aspect of the present invention, the first amplification primer consists essentially of SEQ ID NO:14 and the second amplification primer consists essentially of SEQ ID NO:15.

According to an additional aspect, the present invention provides an oligonucleotide set comprising a first amplification primer and a second amplification primer, the first amplification primer selected from the group consisting of the target binding sequences of SEQ ID NOs:2 and 14 and the second amplification primer selected from the group consisting of the target binding sequences SEQ ID NOs:3 and 15. In another aspect, the first amplification primer consists essentially of the target binding sequence of SEQ ID NO:2 and the second amplification primer consists essentially of the target binding sequence of SEQ ID NO:3. In yet another aspect of the present invention, the first amplification primer consists essentially of the target binding sequence of SEQ ID NO:14 and the second amplification primer consists essentially of the target binding sequence of SEQ ID NO:15.

According to a further aspect, the oligonucleotide set further comprises a signal primer and a reporter probe, the signal primer selected from the group consisting of the target binding sequences of SEQ ID NOs:4, 5, 16 and 17 and the reporter probe selected from the group consisting of SEQ ID NOs:8 and 10. In one aspect, the signal primer consists essentially of the target binding sequence of SEQ ID NO:4 and the reporter probe consists essentially of SEQ ID NO:8. In yet another aspect, the signal primer consists essentially of the target binding sequence of SEQ ID NO:5 and the reporter probe consists essentially of SEQ ID NO:10. According to a further aspect, the oligonucleotide set further comprises a second reporter probe consisting essentially of SEQ ID NO:11. In a further embodiment, the oligonucleotide set with a second reporter probe further comprises one or more bumper primers selected from the group consisting of SEQ ID NOs:1, 12 and 13.

In an additional embodiment, the signal primer consists essentially of the target binding sequence of SEQ ID NO:16 and the reporter probe consists essentially of SEQ ID NO:8. In yet another embodiment of the present invention, the signal primer consists essentially of the target binding sequence of SEQ ID NO:17 and the reporter probe consists essentially of SEQ ID NO:10. In a further aspect, the oligonucleotide set further comprises a second signal primer and a second reporter probe, the second signal primer consisting essentially of SEQ ID NO:17 and the second reporter probe consisting essentially of the hybridization sequence of SEQ ID NO:10. In still another aspect, the oligonucleotide set comprising a second signal primer and a second reporter probe further comprises one or more bumper primers selected from the group consisting of SEQ ID NOs:1, 12 and 13.

According to a further aspect, the target binding sequences of SEQ ID NOs:2, 3, 14 and 15 comprise a sequence required for an amplification reaction. In another embodiment of the present invention, the sequence required for the amplification reaction comprises a restriction endonuclease recognition site that is nickable by a restriction endonuclease. In yet another embodiment, the sequence required for the amplification reaction comprises a promoter recognized by an RNA polymerase. In still another embodiment, the hybridization sequences of SEQ ID NOs:4, 5, 16 and 17 further comprise an indirectly detectable marker. In another aspect, the indirectly detectable marker comprises an adapter sequence.

In a further embodiment, the present invention provides an oligonucleotide comprising a SARS-CoV target sequence selected from the group consisting of SEQ ID NOs:6, 7, 18 and 19.

In another embodiment, the present invention provides a method for detecting the presence or absence SARS-CoV in a sample, the method comprising: (a) treating the sample with a plurality of nucleic acid primers in a nucleic acid amplification reaction wherein a first primer is selected from the group consisting of the target binding sequences of SEQ ID NO:2 and SEQ ID NO:14 and a second primer is selected from the group consisting of the target binding sequences of SEQ ID NO:3 and SEQ ID NO:15; and (b) detecting any amplified nucleic acid product, wherein detection of the amplified product indicates presence of SARS CoV. In a further embodiment, the first primer consists essentially of SEQ ID NO:2 and the second primer consists essentially of SEQ ID NO:3. In yet another embodiment, the first primer consists essentially of SEQ ID NO.: 14 and the second primer consists essentially of SEQ ID NO:15. In still another embodiment, step (a) comprises a Strand Displacement Amplification (SDA) reaction. In a further embodiment, the SDA reaction utilizes one or more bumper primers selected from the group consisting of SEQ ID NOs:1, 12 and 13. In yet another embodiment, the SDA reaction comprises a thermophilic Strand Displacement Amplification (tSDA) reaction. In an additional embodiment, the tSDA reaction is a homogeneous fluorescent real time tSDA reaction. In a further embodiment, step (b) includes the step of hybridizing said amplified nucleic acid product with a signal primer selected from the group consisting of SEQ ID NOs:4, 5, 16 and 17.

According to a further aspect, the present invention provides a method for amplifying a target nucleic acid sequence of SARS-CoV comprising: (a) hybridizing to the nucleic acid (i) a first amplification primer selected from the group consisting of the target binding sequences of SEQ ID NO:2 and 14; and (ii) a second amplification primer selected from the group consisting of the target binding sequences of SEQ ID NO:3 and 15; and (b) extending the hybridized first and second amplification primers on the target nucleic acid sequence whereby the target nucleic acid sequence is amplified. According to a further aspect of the method, the first amplification primer consists essentially of the target binding sequence of SEQ ID NO:2 and the second amplification primer consists essentially of the target binding sequence of SEQ ID NO:3. According to a further aspect of the method, the first amplification primer consists essentially of the target binding sequence of SEQ ID NO:14 and the second amplification primer consists essentially of the target binding sequence of SEQ ID NO:15.

In still another aspect of the method, the target binding sequences of SEQ ID NO:2 and SEQ ID NO:3 comprise a sequence required for an amplification reaction. In another embodiment, the sequence required for the amplification reaction comprises a restriction endonuclease recognition site that is nickable by a restriction endonuclease. In yet another embodiment, the sequence required for the amplification reaction comprises a promoter recognized by an RNA polymerase.

In yet another aspect of the invention, the target binding sequences of SEQ ID NO:14 and SEQ ID NO:15 comprise a sequence required for an amplification reaction. In a further aspect, the sequence required for the amplification reaction comprises a restriction endonuclease recognition site that is nickable by a restriction endonuclease. In a further embodiment, the sequence required for the amplification reaction comprises a promoter recognized by an RNA polymerase.

In a further aspect, the method further comprises indirectly detecting the amplified target nucleic acid by hybridization to a signal primer. In yet another aspect, the signal primer is selected from the group consisting of SEQ ID NOs:4, 5, 16 and 17.

According to a further aspect, the target nucleic acid sequence is selected from the group consisting of SEQ ID NOs:6, 7, 18 and 19.

According to another aspect, the present invention provides a method of quantifying the amount of SARS-CoV nucleic acid in a target sample comprising the steps of: a) combining the target sample with a known concentration of SARS-CoV internal control nucleic acid; b) amplifying the target nucleic acid and internal control nucleic acid in an amplification reaction; c) detecting the amplified nucleic acid; and d) analyzing the relative amounts of amplified SARS-CoV target nucleic acid and internal control nucleic acid. In a further embodiment, step (b) comprises a strand displacement amplification reaction. In yet another embodiment of the method, the SDA reaction comprises a tSDA reaction. According to a further aspect, the amplification reaction utilizes one or more signal primers selected from the group consisting of the hybridization sequences of SEQ ID NOs:4, 5, 16 and 17 and one or more reporter probes selected from the group consisting of the hybridization sequences of SEQ ID NOs:8 and 10 According to yet another aspect, the hybridization sequences of SEQ ID NOs:4, 5, 8, 10, 16 and 17 comprise an indirectly detectable marker. In a further embodiment, the indirectly detectable marker comprises an adapter sequence.

MODES FOR CARRYING OUT THE INVENTION

The methods of the present invention are useful for assaying for the presence of SARS-CoV by the amplification and detection of the SARS-CoV rep sequence. The primers and probes of the present invention are based on portions of the SARS-CoV replicase gene. The present invention also provides oligonucleotides that may be used in amplification, detection and/or quantification of the rep gene. The oligonucleotides may be used in all types of amplification reactions such as, for example, Strand Displacement Amplification (SDA), Polymerase Chain Reaction (PCR), Ligase Chain Reaction, Nucleic Acid Sequence Based Amplification (NASBA), Rolling Circle Amplification (RCA), Transcription Mediated Amplification (TMA) and QB Replicase-mediated amplification. The present invention further provides oligonucleotides that may be used in amplification, detection and/or quantification of the rep gene with sufficient specificity and sensitivity.

The methods of the present invention may be employed, for example, but not by way of limitation, to test clinical specimens obtained from suspected SARS patients. The specimens, or test samples, may be collected from any source suspected of containing SARS nucleic acid. For animals, preferably, mammals, and more preferably, humans, the source of the test samples may include blood, bone marrow, lymph, hard tissues (e.g., liver, spleen, kidney, lung, ovary, etc.), sputum, feces, urine, upper and lower respiratory specimens and other clinical samples. Other sources may include veterinary and environmental samples, as well as in vitro cultures. Those skilled in the art are capable of determining appropriate clinical sources for use in diagnosis of SARS-CoV infection.

DEFINITIONS

The following definitions are provided for reason of clarity, and should not be considered as limiting. Except where noted, the technical and scientific terms used herein are intended to have the same meaning as commonly understood by one of ordinary skill in the art to which the invention pertains.

An "amplification primer" is an oligonucleotide for amplification of a target sequence by extension of the oligonucleotide after hybridization to a target sequence or by ligation of multiple oligonucleotides that are adjacent when hybridized to the target sequence. At least a portion of the amplification primer hybridizes to the target. This portion is referred to as the target binding sequence and it determines target-specificity of the primer. In addition to the target binding sequence, certain amplification methods require specialized non-target binding sequences in the amplification primer. These specialized sequences are necessary for the amplification reaction to proceed and typically serve to append that specialized sequence to the target. For example, but not by of limitation, the amplification primers used in SDA include a restriction endonuclease recognition 5' to the target binding sequence, as disclosed in U.S. Pat. Nos. 5,455,166 and 5,270,184, each of which is incorporated herein by reference. NASBA, Self-Sustaining Sequence Replication (3SR) and transcription-based amplification primers require an RNA polymerase promoter linked to the target binding sequence of the primer. Linking such specialized sequences to a target binding sequence for use in a selected amplification reaction is routine in the art. In contrast, amplification methods such as PCR, which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target whereas a probe may either function by hybridization to the target or through hybridization followed by polymerase-based extension. A hybridized oligonucleotide may function as a probe if it is used to capture or detect a target sequence, and the oligonucleotide may function as a primer when it is employed as a target binding sequence in an amplification primer. It will therefore be appreciated that any of the target binding sequences disclosed herein for amplification, detection or quantification of SARS-CoV may be used either as hybridization probes or as target binding sequences in primers for detection or amplification, optionally linked to a specialized sequence required by the selected amplification reaction or to facilitate detection.

A "bumper" or "external primer" is a primer that anneals to a target sequence upstream of (i.e., 5' to) an amplification primer, such that extension of the external primer displaces the downstream primer and its extension product, i.e., a copy of the target sequence comprising the SDA restriction endonuclease recognition site is displaced. The bumper primers, therefore, consist only of target binding sequences and are designed so that they anneal upstream of the amplification primers and displace them when extended. External primers are designated $B_1$ and $B_2$ by Walker, et al., *Nuc. Acids Res.,* 20:1692-1696 (1992). Extension of external primers is one method for displacing the extension products of amplification primers, but heating may also be suitable in certain cases.

A "reverse transcription primer" also consists only of target binding sequences. It is hybridized at the 3' end of an RNA target sequence to prime reverse transcription of the target. Extension of the reverse transcription primer produces a heteroduplex comprising the RNA target and the cDNA copy of the RNA target produced by reverse transcription. The cDNA is separated from the RNA strand (e.g., by heating, RNase H, or strand displacement) to make it single-stranded and available for amplification. Optionally, a second reverse transcription primer may be hybridized at the 3' end of the target sequence in the cDNA to prime second strand synthesis prior to amplification. Optionally, a reverse transcription primer may also function as an amplification or bumper primer.

The terms "target" and "target sequence" refer to nucleic acid sequences (DNA and/or RNA) to be amplified, replicated or detected. These include the original nucleic acid sequence to be amplified and its complementary second strand, as well as either strand of a copy of the original target sequence produced by amplification or replication of the target sequence. "Amplification products," "extension products" or "amplicons" are oligonucleotides or polynucleotides that comprise copies of the target sequence produced during amplification or replication of the target sequence.

The term "polymerase" refers to any of various enzymes, such as DNA polymerase, RNA polymerase, or reverse transcriptase that catalyze the synthesis of nucleic acids on pre-existing nucleic acid templates. A DNA polymerase assembles the DNA from deoxyribonucleotides, while RNA polymerase assembles the RNA from ribonucleotides.

Based on alignment of 25 SARS-CoV nucleotide sequences, two regions were selected as target sequences for use in amplification of the replicase region, as shown in Tables 1 and 3.

In one embodiment of the present invention, Reverse Transcriptase-Strand Displacement Amplification (RT-SDA) has been adapted for the detection of SARS-CoV replicase RNA in both genomic and subgenomic RNA sequences. SDA is an isothermal (constant temperature) nucleic acid amplification method. In SDA, displacement of single-stranded extension products, annealing of primers to the extension products (or the original target sequence) and subsequent extension of the primers occur concurrently in the reaction mix. Conventional SDA (performed at lower temperatures, usually about 35-45° C.) is described by G. Walker, et al., *Proc. Natl. Acad. Sci. USA* 89:393-396 (1992) and Walker, et al., *Nuc. Acids Res.*, supra. Detection of nucleic acids by SDA is described in detail in U.S. Pat. Nos. 5,455,166; 5,523,204; and 5,916,779, the entire teachings of which are herein incorporated by reference. These patents provide methods for amplification of a target nucleic acid sequence (and its complementary strand) in a sample by endonuclease-mediated strand displacement. Additionally, U.S. Pat. No. 5,916,779 adapts SDA to reverse transcription amplification of RNA targets.

According to the present invention, the SARS-CoV target replicase RNA is extracted from a test sample. The SARS-CoV replicase RNA may be isolated by any method known to those of skill in the art. The replicase RNA is then amplified in, for example, an RT-SDA process. The RT-SDA may be performed as either a one-step process or a two-step process.

The one-step process concurrently generates and amplifies cDNA copies of the SARS-CoV target sequence.

In one embodiment, the one-step RT-SDA process utilizes first amplification and bumper primers designed to allow for incorporation of a restriction endonuclease site and for displacement of single stranded cDNA. The resulting cDNA is subsequently amplified by annealing of second amplification and optionally one or more bumper primers. In another embodiment, the one-step RT-SDA process utilizes a first reverse and optionally one or more bumper primers. Either DNA-dependent DNA polymerase or reverse transcriptase allows for the extension of the cDNA amplified products. In yet another embodiment of the single-step process, a reverse transcriptase enzyme is used to extend one or more of the reverse primers and synthesize cDNA from the RNA template. One of ordinary skill in the art will recognize certain conventional reverse transcriptase enzymes (i.e., AMV, MMLV, Superscript II™) that may be employed in the methods of the present invention.

The foregoing description of the one-step RT-SDA reaction uses SDA amplification primers and bumper primers as an illustrative example. As described in U.S. Pat. No. 5,916,779, however, the reverse transcriptase is capable of performing strand displacement with either SDA primers or reverse transcription primers. Reverse transcription primers may, therefore, also be present for use by the reverse transcriptase in the reverse transcription portion of the reaction. The downstream reverse transcription primer functions as a reverse transcription primer. The upstream reverse transcription primer is similar to an SDA bumper primer, as its extension serves to displace the downstream reverse transcription primer extension product (the cDNA).

Alternatively, the RT-SDA may be a two-step amplification process in which reverse transcription is followed by SDA in discrete steps. Accordingly, a reverse transcription primer is present in the first, reverse transcription step of the reaction. The cDNA is then separated from the RNA template prior to the second, amplification step. The reaction is either heated to separate the DNA:RNA hybrid, or the two strands are separated through chemical or enzymatic means. For example, but not by way of limitation, RNase H or RNase H activity may be used to degrade the RNA strand and thereby create a single strand of DNA. Also, separation of the hybrid can be achieved by the use of a polymerase that lacks 5'→3' activity and displaces one strand from another. SDA primers are added in the second step of the reaction, and SDA amplification proceeds to provide detectable amplification products.

In one embodiment of the two-step process, the reverse primer is an SDA primer, and RNase H activity is endogenous to the reverse transcriptase enzyme. Additionally, the reverse primer may be a bumper primer or a randomly generated DNA sequence. In a further embodiment of the present invention, two-step RT-SDA process is performed using an SDA primer and one or more bumper primers for the reverse transcription reaction. Forward primers and other reaction components necessary for amplification and detection, such as SDA enzymes, deoxyribonucleotides, signal primers, probe(s) and buffer components, are mixed with the products of the RT reaction.

A thermophilic version of the SDA reaction (tSDA) has recently been developed, and this version is performed at a higher, but still constant, temperature using thermostable polymerases and restriction endonucleases, as described in U.S. Pat. Nos. 5,648,211 and 5,744,311, which are incorporated by reference herein. The reaction is performed essentially as conventional SDA, with substitution of a thermostable polymerase and a thermostable restriction endonuclease. The temperature of the reaction is adjusted to a higher temperature suitable for the selected thermophilic enzymes (typically between about 45° C. and 60° C.), and the conventional restriction endonuclease recognition/cleavage site is replaced by the appropriate restriction endonuclease recognition/cleavage site for the selected thermostable endonuclease. Also, in contrast to conventional SDA, the practitioner may include the enzymes in the reaction mixture prior to the initial heat denaturation step if they are sufficiently stable at that temperature.

SDA has been adapted for amplification of nucleic acid target sequences in situ in cells in suspension, on slides or in tissues, with sensitivity and specificity comparable to the in situ PCR. This method is described in detail in U.S. Pat. No. 5,523,204, which is incorporated herein by reference. SDA is gentler to the cells and tissues than is PCR because the SDA reaction is carried out at a constant, lower temperature. In addition, excellent specimen morphology is preserved. In situ amplification by SDA is compatible with immunochemical techniques, so that both amplification of target sequences and immunological staining can be performed on the same specimen.

An RNA-based internal control may be incorporated in the reaction mixture that co-amplifies with the SARS-CoV target sequences of the present invention. The internal control is designed to verify negative results and identify potentially inhibitory samples. Such a control may also be used for the purposes of quantification in a competitive assay format as described by Nadeau et al. *Anal. Biochem.* 276:177-187 (1999). In addition, the use of dried Reverse Transcriptase enzyme may be used in conjunction with the SDA methods described herein. The dried enzyme provides improved workflow over use of liquid enzyme together with a protracted shelf life.

The SDA primers, Bumper Primers and Signal Primers listed in Table 1 and Table 3 were designed for use in RT-SDA reactions in accordance with the methods of the present invention. The binding sequences are underlined. For the SDA Primers, the remaining 5' portion of the sequence comprises the restriction endonuclease recognition site (RERS) required for the SDA reaction to proceed and a generic non-target-specific tail sequence; whereas, for the Signal Primers, the 5' tail comprises a generic non-target-specific sequence which is the same as that of the corresponding reporter probe. It will be readily apparent that the SDA primers may also be used as amplification primers in alternative amplification assays. It will also be apparent that the target binding sequences may be used alone to amplify the target in reactions that do not require specialized sequences or structures (e.g., PCR) and that different specialized sequences required by amplification reactions other than RT-SDA may be substituted for the RERS-containing sequence shown below (e.g., an RNA polymerase promoter). The "F" and "R" in the SDA primer name indicates "forward" and "reverse" primers, respectively, when the oligonucleotides are used in amplification reactions.

TABLE 1

Primers, Probes and Sequences for SARS-CoV Assay Region A

| SEQ ID NO. | Oligonucleotide | Length | 5'-3' Sequence |
|---|---|---|---|
| | BUMPER PRIMERS | | |
| 1 | SarArtB21 * | 21 | CAA CGC TGA GGT GTG TAG GTG |
| 20 | pUC19 Bumper Primer AB | 16 | AAA GGA GGG ATG TGC T |
| | SDA PRIMERS | | |
| 2 | SarAFP | 41 | CGA TTC CGC TCC AGA CTT *CTC GGG* ATA CCA CGT CGC AAT GT |
| 3 | SarARP * | 41 | ACC GCA TCG AAT GCA TGT *CTC GGG* ATG AAG ACC AGT AAT GA |
| | SIGNAL PRIMERS | | |
| 4 | SarAAd-TBD16 | 43 | ACG TTA GCC ACC ATA CGG AT GTC CAG TTA CAT TTT CTG CTT G |
| 5 | SarAAd-MPC | 43 | ACG TTA GCC ACC ATA CTT GA GTC CAG TTA CAT TTT CTG CTT G |
| | TARGET REGION | | |
| 6 | Assay Region A Consensus DNA Target Sequence | 118 | ATA CCA CGT CGC AAT GTG GCT ACA TTA CAA GCA GAA AAT GTA ACT GGA CTT TTT AAG GAC TGT AGT AAG ATC ATT ACT GGT CTT CAT CCT ACA CAG GCA CCT ACA CAC CTC AGC GTT G |
| 7 | Assay Region A Consensus RNA Transcript Sequence | 118 | AUA CCA CGU CGC AAU GUG GCU ACA UUA CAA GCA GAA AAU GUA ACU GGA CUU UUU AAG GAC UGU AGU AAG AUC AUU ACU GGU CUU CAU CCU ACA CAG GCA CCU ACA CAC CUC AGC GUU G |

Primer target hybridization regions are underlined
BsoBI sites are italicized
* May be used to prime reverse transcription

TABLE 2

Reporter Probes for use with SARS-CoV Assays A and B

| SEQ ID NO. | Oligonucleotide | Length | 5'-3'Sequence |
|---|---|---|---|
| | REPORTER PROBE SET A | | |
| 8 | TBD16 (D/R) | 28 | (DABCYL)-T*CC CGA G*T-(ROX)-ACG TTA GCC ACC ATA CGG AT |
| 9 | AltD8 (F/D) | 28 | (FAM)-A*CC CGA G*T-(DABCYL)-AGC TAT CCG CCA TAA GCC AT |
| | REPORTER PROBE SET B | | |
| 10 | MPC (D/R) | 29 | (DABCYL)-T*CC CCG AG*T-(ROX)-ACG TTA GCC ACC ATA CTT GA |
| 11 | MPC2 (F/D) | 29 | (FAM)-T*CC CCG AG*T-(DABCYL)-ACT GAT CCG CAC TAA CGA CT |

Regions that hybridize to the complement of the Signal Primers are underlined (see U.S. Pat. Nos. 6,316,200; 6,743,582; 6,656,680)
BsoBI sites are italicized
ROX: Rhodamine
FAM: Fluorescein

TABLE 3

Primers, Probes and Sequences for SARS-CoV Assay Region B

| SEQ ID NO. | Oligonucleotide | Length | 5'-3' Sequence |
|---|---|---|---|
| BUMPER PRIMERS | | | |
| 12 | SarBrtB17 * | 17 | ATA TTA TGC CAG CCA CC |
| 13 | SarBrtB19 * | 19 | ATA TTA TGC CAG CCA CCG T |
| SDA PRIMERS | | | |
| 14 | SarBFP | 43 | CGT AAT CCG CTC CAG ACT TCT *CGG GAA TAG ACA GTT TCA TCA G* |
| 15 | SarBRP * | 40 | ACC GCA TCG AAT GCA TGT *CTC GGG* TTC CAA TTA CCA CAG T |
| SIGNAL PRIMERS | | | |
| 16 | SarBAd-TBD16 | 40 | ACG TTA GCC ACC ATA CGG ATT GAA GTC AAT AGC CGC CAC T |
| 17 | SarBAd-MPC | 40 | ACG TTA GCC ACC ATA CTT GAT TGA AGT CAA TAG CCG CCA CT |
| TARGET REGION | | | |
| 18 | Assay Region B Consensus DNA Target Sequence | 101 | AAT AGA CAG TTT CAT CAG AAA TTA TTG AAG TCA ATA GCC GCC ACT AGA GGA GCT ACT GTG GTA ATT GGA ACA AGC AAG TTT TAC GGT GGC TGG CAT AAT AT |
| 19 | Assay Region B Consensus RNA Transcript Sequence | 101 | AAU AGA CAG UUU CAU CAG AAA UUA UUG AAG UCA AUA GCC GCC ACU AGA GGA GCU ACU GUG GUA AUU GGA ACA AGC AAG UUU UAC GGU GGC UGG CAU AAU AU |

Primer target hybridization regions are underlined
BsoBI sites are italicized
* May be used to prime reverse transcription Following target amplification, the nucleic acids produced by the methods of the present invention may be detected by any of the methods known in the art for detection of specific nucleic acid sequences. For example, but not by way of limitation, a variety of detection methods for SDA may be used. Several methods for labeling SDA products are discussed in U.S. Pat. No. 6,316,200, the entire teaching of which is herein incorporated by reference. For example, but not by way of limitation, amplification products may be detected by specific hybridization to an oligonucleotide detector probe. The detector probe is a short oligonucleotide that includes a detectable label, i.e., a moiety that generates or can be made to generate a detectable signal. The label may be incorporated into the oligonucleotide probe by nick translation, end-labeling or during chemical synthesis of the probe. Many directly and indirectly detectable labels are known in the art for use with oligonucleotide probes. Directly detectable labels include those labels that do not require further reaction to be made detectable, e.g., radioisotopes, fluorescent moieties and dyes. Indirectly detectable labels include those labels that must be reacted with additional reagents to be made detectable, e.g., enzymes capable of producing a colored reaction product (e.g., alkaline phosphatase (AP) or horseradish peroxidase), biotin, avidin, digoxigenin, antigens, haptens or fluorochromes. The signal from enzyme labels is generally developed by reacting the enzyme with its substrate and any additional reagents required to generate a colored enzymatic reaction product. Biotin (or avidin) labels may be detected by binding to labeled avidin (or labeled biotin) or labeled anti-biotin (or labeled anti-avidin) antibodies. Digoxigenin and hapten labels are usually detected by specific binding to a labeled anti-digoxigenin (anti-dig) or anti-hapten antibody. In general, the detector probe will be selected such that it hybridizes to a nucleotide sequence in the amplicon that is between the binding sites of the two amplification primers. A detector probe may also have the same nucleotide sequence as either of the amplification primers. Methods for detection in vitro and in situ by hybridization to a detector probe are known in the art.

Alternatively, the amplification products of the present invention may be detected by extension of a detector primer as described by Walker, et al., *Nuc. Acids Res.*, supra. In the detector primer extension method, an oligonucleotide primer comprising a detectable label is hybridized to the amplification products and extended by addition of polymerase. For detection, the primer may be 5' end-labeled, for example, using $^{32}$P or a fluorescent label. Alternatively, extension of the hybridized primer may incorporate a dNTP analog comprising a directly or indirectly detectable label. For example, but not by way of limitation, extension of the primer may incorporate a dig-derivatized dNTP, which is then detected after extension by reaction with AP anti-dig and a suitable AP substrate. The primer to be extended may either be the same as an amplification primer or it may be a different primer that hybridizes to a nucleotide sequence in the amplicon that is between the binding sites of the amplification primers.

The detectable label may also be incorporated directly into amplicons during target sequence amplification.

In another embodiment of the invention, RT-SDA products are detected by the methods described in U.S. Pat. No. 6,316, 200 that utilize an unlabelled signal primer comprising a 5' adapter sequence. The 3' end of a reporter probe hybridizes to the complement of the 5' end of the signal primer, producing a 5' overhang. Polymerase fills in the overhang and synthesis of the complement of the reporter probe tail is detected, either directly or indirectly, as an indication of the presence of target. This method utilizes fluorescent energy transfer (FET) rather than the direct detection of fluorescent intensity for detection of hybridization. FET allows for real-time detection of SDA products.

The Signal Primers and Reporter Probes listed in Table 1 through Table 3 were designed for real-time detection of amplification products using the reverse transcriptase products. The structure and use of such primers and probes is described, for example, but not by way of limitation, in U.S. Pat. Nos. 5,547,861, 5,928,869, 6,316,200, 6,656,680 and 6,743,582 each of which is incorporated herein by reference. The hybridization sequences in Tables 1 through Table 3 are underlined. The remaining portions of the Reporter Probe sequences form structures that are typically labeled to facilitate detection of amplification products as is known in the art. It will be readily apparent that the target sequence may be used alone for direct hybridization (typically linked to a detectable label) and that other directly and indirectly labels may be substituted for the hairpin as is known in U.S. Pat. Nos. 5,935,791; 5,846,726; 5,691,145; 5,550,025; and 5,593, 867, the contents of each of which is incorporated herein by reference.

Because the target binding sequence confers target specificity on the primer or probe, it should be understood that the target binding sequences exemplified above for use as particular components of a specified reaction may also be used in a variety of other ways for the detection of SARS-CoV replicase nucleic acid. For example, but not by way of limitation, the target binding sequences of the invention may be used as hybridization probes for direct detection of SARS-CoV, either without amplification or as a post-amplification assay. Such hybridization methods are well-known in the art and typically employ a detectable label associated with or linked to the target binding sequence to facilitate detection of hybridization. Further, essentially all of the target binding sequences set forth above may be used as amplification primers in amplification reaction which do not require additional specialized sequences (such as PCR) or appended to the appropriate specialized for use in 3SR, NASBA, transcription-based or any other primer extension amplification reactions. For detection of amplification products, amplification primers comprising the target binding sequences disclosed herein may be labeled as is known in the art. As an alternative, labeled detector primers comprising the disclosed target binding sequences may be used in conjunction with amplification primers as described in U.S. Pat. Nos. 5,547,861; 5,928,869; 5,593,867; 5,550,025; 5,935,791; 5,888,739; and 5,846,726, each of which is incorporated by reference herein, for real-time homogenous detection of amplification. Such detector primers may comprise a directly or indirectly detectable sequence that does not initially hybridize to the target but which facilitates detection of the detector primer once it has hybridized to the target and has been extended. For example, such detectable sequences may be sequences that form a secondary structure, sequences that contain a restriction site, or linear sequences that are detected by hybridization of their complements to a labeled oligonucleotide (sometimes referred to as a reporter probe) as is known in the art. Alternatively, the amplification products may be detected post-amplification by hybridization of a probe selected from any of the target binding sequences disclosed herein that fall between a selected set of amplification primers.

It is to be understood that an oligonucleotide according to the present invention that consists of a target binding sequence and, optionally, either a sequence required for a selected amplification reaction or a sequence required for a selected detection reaction may also include certain other sequences that serve as spacers, linkers, sequences for labeling or binding of an enzyme, etc. Such additional sequences are typically known to be necessary to obtain optimum function of the oligonucleotide in the selected reaction and are intended to be included by the term "consisting of:"

The present invention also relates to nucleic acid molecules that hybridize under high stringency hybridization conditions (i.e., for selective hybridization) to the nucleotide sequence described herein. "Stringency conditions" refer to the incubation and wash conditions (e.g., temperature, buffer concentration) that determine hybridization of a first nucleic acid to a second nucleic acid. The first and second nucleic acids may be perfectly (100%) complementary, or may be less than perfect (i.e., 70%, 50%, etc.). For example, certain high stringency conditions can be used that distinguish perfectly complementary nucleic acids from those of less complementarity. "High stringency conditions," "moderate stringency conditions" and "low stringency conditions" for nucleic acid hybridizations are explained on pages 2.10.1-2.10.16 and pages 6.3.1-6.3.6 in Current Protocols in Molecular Biology (Ausubel, F. M. et al., John Wiley & Sons (1998), the entire teachings of which are incorporated by reference herein).

Another aspect of the present invention pertains to host cells into which a vector of the invention has been introduced. A host cell can be any prokaryotic or eukaryotic cell. For example, the nucleic acid molecules of the present invention can be expressed in bacterial cells, insect cells, yeast or mammalian cells. Such suitable host cells are known to those skilled in the art.

The invention also provides a pack or kit comprising one or more containers filled with one or more of the ingredients used in the present invention. Optionally associated with such container(s) can be a notice in the form prescribed by a governmental agency regulating the manufacture, use or sale of pharmaceuticals or biological products, which notice reflects approval by the agency for manufacture, use or sale for administration. The pack or kit can be a single unit use of the compositions or it can be a plurality of uses. In particular, the agents can be separated, mixed together in any combination, or present in a single vial The following prophetic examples are provided to illustrate certain embodiments of the invention, but are not intended to limit the invention.

SARS Assay System A Example

RT-SDA for the Detection of SARS-CoV RNA

The following example illustrates the use of the disclosed primers and reporter Probes for the detection of SARS-CoV RNA in clinical samples from patients suspected of infection.

Clinical specimens such as stools, throat swabs and nasopharyngeal aspirates are processed using a QIAGEN QIAamp Viral RNA Mini kit according to the manufacturer's instructions with the addition of an on-column DNase treatment to remove contaminating DNA. For stool specimens, an additional pre-processing step is included to remove particulate matter prior to loading on the QIAGEN columns. Stools are diluted 1:10 with 0.89% saline and centrifuged for 20 min.

at 4,000×g. The supernatant is then decanted and passed through a 0.22 µm filter to remove particulate debris.

One hundred and forty microliters of the clinical sample or stool filtrate are processed through a QIAamp column that is treated with DNase to digest contaminating non-specific DNA bound to the column matrix. After washing to remove the DNase, purified RNA is eluted in a volume of 80 mL water. Thirty microliters of eluate are added to a Priming Microwell containing dried primers, Reporter Probes and nucleotides, followed by 20 µL of Reverse Transcription Buffer containing RNase inhibitor, AMV-RT enzyme and RNA transcripts of an Internal Amplification Control sequence. Final reaction conditions for reverse transcription are as follows: 1500 µM dC$_s$TP; 300 µM each of dATP, dGTP and dTTP; 5 mM magnesium acetate; 1500 nM bumper primer SarArtB21 (SEQ ID NO:1); 300 nM SDA Primer SarARP (SEQ ID NO:3); 1500 nM SDA Primer SarAFP (SEQ ID NO:2); 750 nM Signal Primer SarAAd-MPC (SEQ ID NO:5); 600 nM IAC Signal Primer; 1200 nM Reporter Probe MPC D/R (SEQ ID NO:10); 900 nM Reporter Probe MPC2 F/D (SEQ ID NO:11); 1000 copies of IAC transcript; 5% DMSO; 5% glycerol; 43.5 mM K$_i$PO$_4$; 25 mM KOH; 120 mM bicine; 40 U RNase inhibitor; 10 U AMV-RT. Rehydrated microwells are then incubated at 48° C. for 20 min. before addition of 100 µL of SDA Buffer and transfer to a 72° C. heat block. At the same time, Amplification Microwells containing dried SDA enzymes (Bst polymerase and BsoBI restriction enzyme) are pre-warmed at 54° C. After a 10 min. incubation, 100 µL of sample are transferred from the Priming Microwells to the Amplification Microwells, which are then sealed and incubated in a BD ProbeTec ET reader at 52.5° C. Final reaction conditions for SDA are as follows: 500 µM dC$_s$TP; 100 µM each of dATP, dGTP and dTTP; 5.7 mM magnesium acetate; 1500 nM Bumper Primer SarArtB21 (SEQ ID NO:1); 100 nM SDA Primer SarARP (SEQ ID NO:3); 500 nM SDA Primer SarAFP (SEQ ID NO:2); 250 nM Signal Primer SarAAd-MPC (SEQ ID NO:5); 200 nM IAC Signal Primer; 400 nM Reporter Probe MPC D/R (SEQ ID NO:10); 300 nM IAC Reporter Probe MPC2 F/D (SEQ ID NO:11); 12.5% DMSO; 1.67% glycerol; 24.55 mM K$_i$PO$_4$; 82 mM KOH; 143 mM bicine; 12 U Bst polymerase; 45 U BsoBI restriction enzyme.

During the course of a 1 hour incubation, fluorescent readings are taken every minute in both optical channels of the BD ProbeTec ET instrument and results are reported in terms of the PAT scores for the SARS-CoV target and IAC. Reactions in which the fluorescent readings never achieve the predetermined threshold of fluorescence are assigned a PAT score of 0. Reactions that yielded ROX PAT scores >0, corresponding to the MPC D/R Reporter Probe (SEQ ID NO:10), are considered positive for SARS-CoV, while reactions that yield FAM PAT scores >0, corresponding to the IAC Reporter Probe MPC2 F/D (SEQ ID NO:11), are considered positive for IAC. Those in which neither the FAM nor ROX signals achieve their respective thresholds (PAT scores=0) are considered indeterminate. External positive and negative controls are included in each assay run to verify performance. These controls are required to yield the positive and negative correct results respectively in order for the results from patient specimens to be reported by the instrument.

Anticipated Results and Conclusions

Specimens from infected patients that contain SARS-CoV in sufficient quantity to be above the limit of detection of the assay would yield positive results (i.e., ROX PAT scores >0). Specimens from uninfected patients or from those whose clinical load is below the analytical sensitivity of the assay would yield negative results (i.e., ROX PAT score=0). Contamination of reagents with RNase or procedural error would be indicated by a failure of the IAC to amplify (i.e., FAM PAT score=0). A summary of possible results is presented in Table 4.

TABLE 4

Summary of possible result outcomes for the BD ProbeTec ET SARS-CoV assay

| PAT Score | | |
|---|---|---|
| SARS-CoV Target (ROX) | IAC (FAM) | Reported Result |
| >0 | Any | Positive for SARS-CoV |
| 0 | 0 | Indeterminate |
| 0 | >0 | Negative for SARS-CoV or virus present below the analytical sensitivity of the assay |

SARS Assay System B Example

RT-SDA for the Detection of SARS-CoV RNA

The following example illustrates the use of the disclosed primers and reporter Probes for the detection of SARS-CoV RNA in clinical specimens.

Clinical specimens such as stool samples, throat swabs and nasopharyngeal aspirates are processed using a QIAGEN QIAamp Viral RNA Mini kit according to the manufacturer's instructions with the addition of an on-column DNase treatment to remove contaminating DNA. For stool specimens, an additional pre-processing step is included to remove particulate matter prior to loading on the QIAGEN columns. Stools are diluted 1:10 with 0.89% saline and centrifuged for 20 min. at 4,000×g. The supernatant is then decanted and passed through a 0.22 µm filter to remove particulate debris.

One hundred and forty microliters of the sample or stool filtrate are processed through a QIAamp column that is treated with DNase to digest contaminating non-specific DNA bound to the column matrix. After washing to remove the DNase, purified RNA is eluted in a volume of 80 µL water. Thirty microliters of eluate are added to a Priming Microwell containing dried primers, Reporter Probes and nucleotides, followed by 20 µL of Reverse Transcription Buffer containing RNase inhibitor, AMV-RT enzyme and RNA transcripts of an Internal Amplification Control sequence. Final reaction conditions for reverse transcription are as follows: 1500 µM dC$_s$TP; 300 µM each of dATP, dGTP and dTTP; 5 mM magnesium acetate; 1500 nM Bumper Primer SarBrtB19 (SEQ ID NO:13); 1500 nM SDA Primer SarBRP (SEQ ID NO:15); 300 nM SDA Primer SarBFP (SEQ ID NO:14); 750 nM Signal Primer SarBAd-MPC (SEQ ID NO:17); 600 nM IAC Signal Primer; 1200 nM Reporter Probe MPC D/R (SEQ ID NO:10); 900 nM IAC Reporter Probe MPC2 F/D (SEQ ID NO:11); 1000 copies of IAC transcript; 5% DMSO; 5% glycerol; 43.5 mM K$_i$PO$_4$; 25 mM KOH; 120 mM bicine; 40 U RNase inhibitor; 10 U AMV-RT. Rehydrated microwells are then incubated at 48° C. for 20 min. before addition of 100 µL of SDA Buffer and transfer to a 72° C. heat block. At the same time, Amplification Microwells containing dried SDA enzymes (Bst polymerase and BsoBI restriction enzyme) are placed at 52° C. After a 10 min. incubation, 100 µL of sample are transferred from the Priming Microwells to the Amplification Microwells, which are then sealed and incubated in a BD ProbeTec ET reader at 52.5° C. Final reaction conditions for SDA are as follows: 500 μM dC$_s$TP; 100 μM each of dATP, dGTP and dTTP; 5.7 mM magnesium acetate; 500 nM Bumper Primer SarBrtB19 (SEQ ID NO:13); 500 nM SDA Primer SarBRP (SEQ ID NO:15); 100 nM SDA Primer SarBFP (SEQ ID NO:14); 250 nM Signal Primer SarBAd-MPC (SEQ ID NO:17); 200 nM IAC Signal Primer; 400 nM Reporter Probe MPC D/R (SEQ ID NO:10); 300 nM IAC Reporter Probe MPC2 F/D (SEQ ID NO:11); 12.5% DMSO; 1.67% glycerol; 24.5 mM K$_i$PO$_4$; 82 mM KOH; 143 mM bicine; 12 U Bst polymerase; 45 U BsoBI restriction enzyme.

During the course of a 1 hour incubation, fluorescent readings are taken every minute in both optical channels of the BD ProbeTec ET instrument and results are reported in terms of the PAT scores for the SARS-CoV target and IAC. Reactions in which the fluorescent readings never achieve the predetermined threshold of fluorescence are assigned a PAT score of 0. Reactions that yielded ROX PAT scores >0, corresponding to the MPC D/R Reporter Probe (SEQ ID NO:10), are considered positive for SARS-CoV, while reactions that yield FAM PAT scores >0, corresponding to the IAC Reporter Probe MPC2 F/D (SEQ ID NO:11), are considered positive for IAC. Those in which neither the FAM nor ROX signals achieve their respective thresholds (PAT scores=0) are considered indeterminate. External positive and negative controls are included in each assay run to verify performance. These controls are required to yield the positive and negative correct results respectively in order for the results from patient specimens to be reported by the instrument.

Anticipated Results and Conclusions

Specimens from infected patients that contain SARS-CoV in sufficient quantity to be above the limit of detection of the assay would yield positive results (i.e., ROX PAT scores >0). Specimens from uninfected patients or from those whose clinical load is below the analytical sensitivity of the assay would yield negative results (i.e., ROX PAT score=0). Contamination of reagents with RNase or procedural error would be indicated by a failure of the IAC to amplify (i.e., FAM PAT score=0). A summary of possible results is presented in Table 5.

TABLE 5

Summary of possible result outcomes for the BD ProbeTec ET SARS-CoV assay

| PAT Score | | |
| --- | --- | --- |
| SARS-CoV Target (ROX) | IAC (FAM) | Reported Result |
| >0 | Any | Positive for SARS-CoV |
| 0 | 0 | Indeterminate |
| 0 | >0 | Negative for SARS-CoV or virus present below the analytical sensitivity of the assay |

The following experimental examples are provided to illustrate certain embodiments of the invention, but are not intended to limit the invention.

SARS ASSAY SYSTEM A EXAMPLES

Example 1

DNA Amplification Using SARS-CoV-Specific Primers

Part A:

The ability of the disclosed combination of primers and probes to amplify SARS-CoV nucleic acid was demonstrated using a plasmid DNA clone of the target sequence corresponding to nucleotides 17936-18024 of SARS-CoV strain BJ03 (GenBank Accession No. AY278490). Linearized plasmid DNA was quantified using PicoGreen® dsDNA Quantitation Reagent (Molecular Probes, Inc., Eugene, Oreg.) and diluted to a working concentration with water containing 7 ng/mL salmon sperm DNA. Four replicate SDA reactions were run at each of six target levels, including negative controls that contained water in place of target DNA.

In brief, DNA target was added to SDA Buffer and denatured by heating in a boiling water bath for 5 min. One hundred and ten microliters of the denatured sample was then added to Priming Microwells containing 40 μL of a solution of SDA Primers, Reporter Probe and nucleotides. Following an incubation at ambient temperature for 20 min., the Priming Microwells were transferred to a heat block at 72° C., while corresponding Amplification Microwells containing dried Bst polymerase and BsoBI restriction enzyme were pre-warmed at 54° C. After 10 min. incubation, 10 μL of the priming mixture were transferred from the Priming to the Amplification Microwells, which were then sealed and loaded into a BD ProbeTec ET reader set at 52.5° C. Fluorescent signals were monitored over the course of 1 hour and analyzed using the Passes After Threshold (PAT) algorithm developed for this instrument. (Wolfe D M, Wang S S, Thornton K, Kuhn A M, Nadeau J G, Hellyer T J. Homogeneous strand displacement amplification. In: DNA amplification—current technologies and applications, Demidov V V and Broude N E (Eds.), Horizon Bioscience, Wymondham, UK.) The PAT scores represent the number of instrument passes remaining after the fluorescent readings achieve a pre-defined threshold value. Final SDA reaction conditions were as follows: 50 nM pUC19-based Bumper Primer AB (SEQ ID NO:20); 100 nM SDA Primer SarARP (SEQ ID NO:3); 500 nM SDA Primer SarAFP (SEQ ID NO:2); 250 nM Signal Primer SarAAd-TBD16 (SEQ ID NO:4); 500 nM Reporter Probe TBD16 D/R (SEQ ID NO:8); 500 μM deoxycytidine 5'-O-(1-Thiotriphosphate), S-isomer (dC$_s$TP); 100 μM each of dATP, dGTP and dTTP; 12.5% DMSO; 25 mM K$_i$PO$_4$; 82 mM KOH; 143 mM bicine; 12 U Bst polymerase; 30 U BsoBI restriction enzyme; 5 mM magnesium acetate.

Results and Conclusions

Positive results were obtained with as little 25 copies of the target plasmid per reaction while no false-positive results were observed in any of the negative controls (Table 6). These data demonstrate that the disclosed combination of primers and Reporter Probe is capable of detecting a SARS-CoV-specific nucleic acid target sequence with a high degree of analytical sensitivity.

TABLE 6

Amplification and detection of a SARS-CoV-specific target sequence

| Target Level Per Reaction | PAT Score | | | | |
|---|---|---|---|---|---|
| | A | B | C | D | Mean |
| 10000 | 52 | 51 | 49 | 51 | 51 |
| 1000 | 52 | 51 | 50 | 51 | 51 |
| 500 | 50 | 47 | 44 | 50 | 48 |
| 100 | 50 | 49 | 50 | 49 | 49 |
| 50 | 37 | 0 | 0 | 43 | 20 |
| 25 | 35 | 47 | 0 | 47 | 32 |
| 0 | 0 | 0 | 0 | 0 | 0 |

PAT scores: 0 = Negative; >0 = Positive

Part B:

A second experiment was conducted to demonstrate the analytical sensitivity of the disclosed primers for the detection of SARS-CoV-specific nucleic acid. In contrast to the previous experiment, Reporter Probe MPC D/R (SEQ ID NO:10) was used together with Signal Primer SarAAd-MPC (SEQ ID NO:5).

Briefly, DNA target was added to SDA Buffer and denatured by heating in a boiling water bath for 5 min. One hundred and ten microliters of the denatured sample was then added to Priming Microwells containing 40 μL of a solution of SDA Primers, Reporter Probe and nucleotides. The Priming Microwells were allowed to sit for 20 min. at ambient temperature, before being transferred to a heat block at 72° C. At the same time, corresponding Amplification Microwells containing dried Bst polymerase and BsoBI restriction enzyme were pre-warmed at 54° C. Following a 10 min. incubation, 100 μL of the priming mixture were transferred from the Priming to the Amplification Microwells, which were then sealed and placed at 52.5° C. in a BD ProbeTec ET reader. Fluorescent signals were monitored over the course of 1 hour and analyzed using the PAT algorithm developed for this instrument. The PAT scores represent the number of instrument passes remaining after the fluorescent readings achieve a pre-defined threshold value. Final SDA reaction conditions were as follows: 50 nM pUC19-based Bumper Primer AB (SEQ ID NO:20); 100 nM SDA Primer SarARP (SEQ ID NO:3); 500 nM SDA Primer SarAFP (SEQ ID NO:2); 250 nM Signal Primer SarAAd-MPC (SEQ ID NO:5); 500 nM Reporter Probe MPC D/R (SEQ ID NO:10); 500 μM $dC_sTP$; 100 μM each of dATP, dGTP and dTTP; 12.5% DMSO; 25 mM $K_iPO_4$; 82 mM KOH; 143 mM bicine; 12 U Bst polymerase; 30 U BsoBI restriction enzyme; 5 mM magnesium acetate.

Results and Conclusions

Results are summarized in Table 7. All reactions containing 100 copies of plasmid DNA were positive. In contrast, none of the reactions containing water in place of plasmid DNA yielded positive results, thereby demonstrating the analytical sensitivity and specificity of the disclosed of primers and Reporter Probe combination for the detection of the SARS-CoV-specific nucleic acid target sequence.

TABLE 7

Amplification and detection of a SARS-CoV-specific target sequence using MPC D/R Reporter Probe

| | PAT Score | |
|---|---|---|
| Replicate | 100 Targets Per Reaction | Negative Control |
| A | 47.8 | 0 |
| B | 47.9 | 0 |
| C | 47.7 | 0 |
| D | 48.0 | 0 |
| E | 45.9 | 0 |
| F | 46.0 | 0 |
| G | 49.2 | 0 |
| H | 47.6 | 0 |
| Mean | 47.5 | 0 |

PAT scores: 0 = Negative; >0 = Positive

Example 2

Analytical Specificity

The analytical specificity of the disclosed primers and probes was verified by testing a panel of 43 bacteria and fungi that are likely to be found in respiratory and/or gastrointestinal specimens. Because all these organisms have genomes comprised of DNA rather than RNA, no reverse transcription step was included in these reactions. A suspension of each organism was prepared in Phosphate-Buffered Saline containing Bovine Serum Albumin (PBS/BSA) at a concentration of approximately $10^7$-$10^8$ cells/mL. Fifteen microliters of each suspension were mixed with 150 μL SDA Buffer and heated in a boiling water bath for 5 min. to lyse the organisms and denature the DNA. After cooling to room temperature, 110 μL of denatured sample were added to a Priming Microwell containing 40 μL of a solution of SDA Primers, Reporter Probe and nucleotides. The Priming Microwells were incubated at ambient temperature for 20 min. and then transferred to a heat block at 72° C., while corresponding Amplification Microwells were pre-warmed at 54° C. After 10 min., 100 μL of the priming mixture were transferred from the Priming to the Amplification Microwells, which were then sealed and loaded into a BD ProbeTec ET reader set at 52.5° C. Fluorescence was monitored over the course of 1 hour and analyzed using the PAT algorithm developed for this instrument. Final SDA conditions were as follows: 50 nM pUC19-based Bumper Primer AB (SEQ ID NO:20); 100 nM SDA Primer SarARP (SEQ ID NO:3); 500 nM SDA Primer SarAFP (SEQ ID NO:2); 250 nM Signal Primer SarAAd-TBD16 (SEQ ID NO:4); 500 nM Reporter Probe TBD16 D/R (SEQ ID NO:8); 500 μM $dC_sTP$; 100 μM each of dATP, dGTP and dTTP; 12.5% DMSO; 25 mM $K_iPO_4$; 82 mM KOH; 143 mM bicine; 12 U Bst polymerase; 30 U BsoBI restriction enzyme; 5 mM magnesium acetate.

Results and Conclusions

Results are summarized in Table 8. No positive results were obtained except from a plasmid clone of the SARS-CoV target sequence that was run as a positive control, thereby demonstrating the specificity of the disclosed primers and Reporter Probe for the detection of SARS-CoV.

TABLE 8

Panel of bacteria and fungi tested with the BD ProbeTec ET SARS-CoV assay

| Species | Strain | PAT Score | Result |
|---|---|---|---|
| Acinetobacter calcoaceticus | BD 13339 | 0 | Negative |
| Actinomyces israelii | ATCC 10049 | 0 | Negative |
| Aeromonas hydrophila | ATCC 7966 | 0 | Negative |
| Alcaligenes faecalis | ATCC 8750 | 0 | Negative |
| Bacteroides fragilis | ATCC 25285 | 0 | Negative |
| Bordetella pertussis | ATCC 9797 | 0 | Negative |
| Candida albicans | ATCC 44808 | 0 | Negative |
| Chlamydophila pneumoniae | AR-39 | 0 | Negative |
| Citrobacter freundii | ATCC 8090 | 0 | Negative |
| Corynebacterium diphtheriae | ATCC 11913 | 0 | Negative |
| Corynebacterium jeikeium | ATCC 43734 | 0 | Negative |
| Cryptococcus neoformans | ATCC 36556 | 0 | Negative |
| Edwardsiella tarda | ATCC 15469 | 0 | Negative |
| Eikenella corrodens | ATCC 23834 | 0 | Negative |
| Enterobacter aerogenes | ATCC 13048 | 0 | Negative |
| Enterococcus faecalis | ATCC 29212 | 0 | Negative |
| Escherichia coli | ATCC 11775 | 0 | Negative |
| Fusobacterium nucleatum | ATCC 25586 | 0 | Negative |
| Haemophilus influenzae | ATCC 33533 | 0 | Negative |
| Haemophilus parainfluenzae | ATCC 7901 | 0 | Negative |
| Kingella kingae | ATCC 23330 | 0 | Negative |
| Klebsiella pneumoniae subsp. pneumoniae | ATCC 13883 | 0 | Negative |
| Lactobacillus acidophilus | ATCC 4356 | 0 | Negative |
| Legionella pneumophila | ATCC 33152 | 0 | Negative |
| Morganella morganii | ATCC 25830 | 0 | Negative |
| Neisseria mucosa | ATCC 19696 | 0 | Negative |
| Peptostreptococcus anaerobius | ATCC 27337 | 0 | Negative |
| Plesiomonas shigelloides | ATCC 14029 | 0 | Negative |
| Porphyromonas asaccharolytica | ATCC 25260 | 0 | Negative |
| Proteus mirabilis | ATCC 29906 | 0 | Negative |
| Pseudomonas aeruginosa | ATCC 27853 | 0 | Negative |
| Serratia marcescens | ATCC 8100 | 0 | Negative |
| Staphylococcus aureus | ATCC 12598 | 0 | Negative |
| Staphylococcus epidermidis | ATCC E155 | 0 | Negative |
| Stenotrophomonas maltophila | ATCC 13637 | 0 | Negative |
| Streptococcus mutans | ATCC 25175 | 0 | Negative |
| Streptococcus pneumoniae | ATCC 6303 | 0 | Negative |
| Streptococcus pyogenes | ATCC 19615 | 0 | Negative |
| Veillonella parvula | ATCC 10790 | 0 | Negative |
| Yersinia enterolitica | ATCC 27729 | 0 | Negative |
| Yersinia ruckeri | Not known | 0 | Negative |
| SARS-CoV Positive Control | Not Applicable | 44.7 | Positive |
| SARS-CoV Positive Control | Not Applicable | 41.1 | Positive |
| SARS-CoV Positive Control | Not Applicable | 23.7 | Positive |
| SARS-CoV Positive Control | Not Applicable | 43.3 | Positive |
| SARS-CoV Negative Control | Not Applicable | 0 | Negative |
| SARS-CoV Negative Control | Not Applicable | 0 | Negative |
| SARS-CoV Negative Control | Not Applicable | 0 | Negative |
| SARS-CoV Negative Control | Not Applicable | 0 | Negative |

BD: BD Diagnostics
ATCC: American Type Culture Collection
PAT scores >0 were considered positive

SARS ASSAY SYSTEM B EXAMPLES

Example 1

DNA Amplification Using SARS-CoV-Specific Primers

The ability of the disclosed combination of primers and probes to amplify SARS-CoV nucleic acid was demonstrated using a plasmid DNA clone of the target sequence corresponding to nucleotides 15068-15138 of SARS-CoV strain BJ03 (GenBank Accession No. AY278490). Linearized plasmid DNA was quantified using PicoGreen dsDNA Quantitation Reagent (Molecular Probes, Inc., Eugene, Oreg.) and diluted to a working concentration with water containing 7 ng/µL salmon sperm DNA. Eight replicate SDA reactions were run at each of three target levels, including negative controls that contained water in place of target DNA.

In brief, DNA target was added to SDA Buffer and denatured for by heating in a boiling water bath for 5 min. One hundred and fifty microliters of the denatured sample was then added to Priming Microwells containing dried SDA Primers, Reporter Probe and nucleotides. Following an incubation at ambient temperature for 20 min., the Priming Microwells were transferred to a heat block at 72° C., while corresponding Amplification Microwells containing dried Bst polymerase and BsoBI restriction enzyme were prewarmed at 54° C. After 10 min., 100 µL of the priming mixture were transferred from the Priming to the Amplification Microwells, which were then sealed and loaded into a BD ProbeTec ET reader set at 52.5° C. Fluorescent signals were monitored over the course of 1 hour and analyzed using the PAT algorithm developed for this instrument. The PAT scores represent the number of instrument passes remaining after the fluorescent readings achieve a pre-defined threshold value. Final SDA reaction conditions were as follows: 50 nM pUC19-based Bumper Primer AB (SEQ ID NO:20); 500 nM SDA Primer SarBRP (SEQ ID NO:15); 100 nM SDA Primer SarBFP (SEQ ID NO:14); 250 nM Signal Primer SarBAdMPC (SEQ ID NO:17); 300 nM Reporter Probe MPC D/R (SEQ ID NO:10); 500 mM deoxycytidine 5'-O-(1-Thiotriphosphate), S-isomer ($dC_sTP$); 100 µM each of dATP, dGTP and dTTP; 12.5% DMSO; 25 mM $K_iPO_4$; 82 mM KOH; 143 mM bicine; 12 U Bst polymerase; 30 U BsoBI restriction enzyme; 5 mM magnesium acetate.

Results and Conclusions

Positive results were obtained with as little 15 copies of the target plasmid per reaction while no false-positive results were observed in any of the negative controls (Table 9). These data demonstrate that the disclosed combination of primers and Reporter Probe is capable of detecting the targeted SARS-CoV-specific nucleic acid sequence with a high degree of analytical sensitivity.

TABLE 9

Amplification and detection of a SARS-CoV-specific target sequence

| | PAT Score | | |
|---|---|---|---|
| Replicate | Negative Control | 15 Targets Per Reaction | 75 Targets Per Reaction |
| A | 0 | 42 | 47 |
| B | 0 | 42 | 47 |
| C | 0 | 46 | 48 |
| D | 0 | 48 | 48 |
| E | 0 | 45 | 48 |
| F | 0 | 46 | 49 |
| G | 0 | 47 | 49 |
| H | 0 | 43 | 45 |
| Mean | 0 | 45 | 48 |

PAT scores: 0 = Negative; >0 = Positive

Example 2

Analytical Specificity

The analytical specificity of the disclosed primers and probes was verified by testing a panel of 43 bacteria and fungi that are likely to be found in respiratory and/or gastrointestinal specimens. Because all these organisms have genomes comprised of DNA rather than RNA, no reverse transcription step was included in these reactions. A suspension of each organism was prepared in PBS/BSA at a concentration of approximately $10^7$-$10^8$ cells/mL. Fifteen microliters of each suspension were mixed with 150 μL SDA Buffer and heated in a boiling water bath for 5 min. to lyse the organisms and denature the DNA. After cooling to room temperature, 110 μL of denatured sample were added to a Priming Microwell containing 40 μL of a solution of SDA Primers, Reporter Probe and nucleotides. The Priming Microwells were allowed to sit at ambient temperature for 20 min. and then transferred to a heat block at 72° C., while corresponding Amplification Microwells were pre-warmed at 54° C. After a 10 min. incubation, 100 μL of the priming mixture were transferred from the Priming to the Amplification Microwells, which were then sealed and loaded into a BD ProbeTec ET reader set at 52.5° C. Fluorescence was monitored over the course of 1 hour and analyzed using the PAT algorithm developed for this instrument. Final SDA conditions were as follows: 50 nM pUC19-based Bumper Primer AB (SEQ ID NO:20); 500 nM SDA Primer SarBRP (SEQ ID NO:15); 100 nM SDA Primer SarBFP (SEQ ID NO:14); 250 nM Signal Primer SarBAd-MPC (SEQ ID NO:17); 500 nM Reporter Probe MPC D/R (SEQ ID NO:10); 500 mM $dC_sTP$; 100 μM each of dATP, dGTP and dTTP; 12.5% DMSO; 25 mM KiPO4; 82 mM KOH; 143 mM bicine; 12 U Bst polymerase; 30 U BsoBI restriction enzyme; 5 mM magnesium acetate.

Results and Conclusions

As illustrated in Table 10, no positive results were obtained except from a plasmid clone of the SARS-CoV target sequence that was run as a positive control. This demonstrates the specificity of the disclosed primers and Reporter Probe for the detection of SARS-CoV.

TABLE 10

Panel of bacteria and fungi tested with the BD ProbeTec ET SARS-CoV assay

| Species | Strain | PAT Score | Result |
|---|---|---|---|
| Acinetobacter calcoaceticus | BD 13339 | 0 | Negative |
| Actinomyces israelii | ATCC 10049 | 0 * | Negative |
| Aeromonas hydrophila | ATCC 7966 | 0 | Negative |
| Alcaligenes faecalis | ATCC 8750 | 0 | Negative |
| Bacteroides fragilis | ATCC 25285 | 0 | Negative |
| Blastomyces dermatitidis | ATCC 4292 | 0 | Negative |
| Bordetella pertussis | ATCC 9797 | 0 | Negative |
| Branhamella catarrhalis | ATCC 25238 | 0 | Negative |
| Candida albicans | ATCC 44808 | 0 | Negative |
| Chlamydophila pneumoniae | AR-39 | 0 | Negative |
| Citrobacter freundii | ATCC 8090 | 0 | Negative |
| Clostridium perfringens | ATCC 13124 | 0 | Negative |
| Corynebacterium diphtheriae | ATCC 11913 | 0 | Negative |
| Corynebacterium jeikeium | ATCC 43734 | 0 | Negative |
| Cryptococcus neoformans | ATCC 36556 | 0 | Negative |
| Edwardsiella tarda | ATCC 15469 | 0 | Negative |
| Eikenella corrodens | ATCC 23834 | 0 | Negative |

TABLE 10-continued

Panel of bacteria and fungi tested with the BD ProbeTec ET SARS-CoV assay

| Species | Strain | PAT Score | Result |
|---|---|---|---|
| Enterobacter aerogenes | ATCC 13048 | 0 | Negative |
| Enterococcus faecalis | ATCC 29212 | 0 | Negative |
| Escherichia coli | ATCC 11775 | 0 | Negative |
| Fusobacterium nucleatum | ATCC 25586 | 0 | Negative |
| Haemophilus influenzae | ATCC 33533 | 0 | Negative |
| Haemophilus parainfluenzae | ATCC 7901 | 0 | Negative |
| Histoplasma capsulatum | ATCC 12700 | 0 | Negative |
| Kingella kingae | ATCC 23330 | 0 | Negative |
| Klebsiella pneumoniae subsp. pneumoniae | ATCC 13883 | 0 | Negative |
| Lactobacillus acidophilus | ATCC 4356 | 0 | Negative |
| Legionella pneumophila | ATCC 33152 | 0 | Negative |
| Moraxella osloensis | ATCC 19976 | 0 | Negative |
| Morganella morganii | ATCC 25830 | 0 | Negative |
| Mycobacterium tuberculosis | ATCC 27294 | 0 | Negative |
| Mycoplasma pneumoniae | ATCC 29342 | 0 | Negative |
| Neisseria meningitides | ATCC 13077 | 0 | Negative |
| Neisseria mucosa | ATCC 19696 | 0 | Negative |
| Peptostreptococcus anaerobius | ATCC 27337 | 0 | Negative |
| Plesiomonas shigelloides | ATCC 14029 | 0 | Negative |
| Porphyromonas asaccharolytica | ATCC 25260 | 0 | Negative |
| Proteus mirabilis | ATCC 29906 | 0 | Negative |
| Providencia stuartii | ATCC 35031 | 0 | Negative |
| Pseudomonas aeruginosa | ATCC 27853 | 0 | Negative |
| Serratia marcescens | ATCC 8100 | 0 | Negative |
| Salmonella cholerasuis | ATCC 13076 | 0 | Negative |
| Staphylococcus aureus | ATCC 12598 | 0 | Negative |
| Staphylococcus epidermidis | ATCC E155 | 0 | Negative |
| Stenotrophomonas maltophila | ATCC 13637 | 0 | Negative |
| Streptococcus mitis | ATCC 6249 | 0 | Negative |
| Streptococcus mutans | ATCC 25175 | 0 | Negative |
| Streptococcus pneumoniae | ATCC 6303 | 0 | Negative |
| Streptococcus pyogenes | ATCC 19615 | 0 | Negative |
| Veillonella parvula | ATCC 10790 | 0 | Negative |
| Vibrio parahaemolyticus | ATCC 17802 | 0 | Negative |
| Yersinia enterolitica | ATCC 27729 | 0 | Negative |
| SARS-CoV Positive Control | Not Applicable | 51 | Positive |
| SARS-CoV Positive Control | Not Applicable | 50 | Positive |
| SARS-CoV Positive Control | Not Applicable | 51 | Positive |
| SARS-CoV Positive Control | Not Applicable | 50 | Positive |
| SARS-CoV Negative Control | Not Applicable | 0 | Negative |
| SARS-CoV Negative Control | Not Applicable | 0 | Negative |
| SARS-CoV Negative Control | Not Applicable | 0 | Negative |
| SARS-CoV Negative Control | Not Applicable | 0 | Negative |

* Negative upon repeat testing; initial result positive (PAT score = 48) due to laboratory contamination
BD: BD Diagnostics
ATCC: American Type Culture Collection
PAT scores >0 were considered positive

The invention claimed is:

1. An oligonucleotide set comprising a first amplification primer and a second amplification primer, the first amplification primer comprising SEQ ID NO:2 and the second amplification primer comprising SEQ ID NO: 3.

2. The oligonucleotide set of claim 1, further comprising a signal primer and a reporter probe, the signal primer comprising the target binding sequence of SEQ ID NOs:4, 5, 16 or 17 and the reporter probe comprising SEQ ID NOs:8 or 10.

3. The oligonucleotide set of claim 2, wherein the signal primer comprises the target binding sequence of SEQ ID NO:4 and the reporter probe comprises SEQ ID NO:8, the signal primer comprises the target binding sequence of SEQ ID NO:5 and the reporter probe comprises SEQ ID NO:10, the signal primer comprises the target binding sequence of SEQ ID NO:16 and the reporter probe comprises SEQ ID NO:8, the signal primer comprises the target binding sequence of SEQ ID NO:17 and the reporter probe comprises SEQ ID NO:10.

4. The oligonucleotide set of claim 2, further comprising one or more bumper primers comprising SEQ ID NOs:1, 12 or 13.

5. The oligonucleotide set of claim 3, wherein the signal primer comprises the target binding sequence of SEQ ID NO:5 and the reporter probe comprises SEQ ID NO:10 and further comprising a second reporter probe comprising SEQ ID NO:11.

6. The oligonucleotide set of claim 5, further comprising one or more bumper primers comprising SEQ ID NOs:1, 12 or 13.

7. The oligonucleotide set of claim 3, wherein the signal primer comprises the target binding sequence of SEQ ID NO:17 and the reporter probe comprises SEQ ID NO:10 and further comprising a second signal primer and a second reporter probe, the second signal primer comprising SEQ ID NO:17 and the second reporter probe comprising the hybridization sequence of SEQ ID NO:10.

8. The oligonucleotide set of claim 7, further comprising one or more bumper primers comprising SEQ ID NOs:1, 12 or 13.

9. The oligonucleotide set of claim 2, wherein the hybridization sequences of SEQ ID NOs:4, 5, 8, 9, 10, 11, 16 and 17 further comprise an indirectly detectable marker.

10. The oligonucleotide set of claim 9 wherein the indirectly detectable marker is comprises an adapter sequence.

11. A method for detecting the presence or absence SARS-CoV in a sample, the method comprising: (a) treating the sample with a plurality of nucleic acid primers in a nucleic acid amplification reaction wherein a first primer comprises the target binding sequence of SEQ ID NO:2 and a second primer comprises the target binding sequence of SEQ ID NO:3; and (b) detecting any amplified nucleic acid product, wherein detection of the amplified product indicates presence of SARS-CoV.

12. The method of claim 11 wherein step (a) comprises a Strand Displacement Amplification (SDA) reaction.

13. The method of claim 12 wherein the SDA reaction utilizes one or more bumper primers comprising SEQ ID NOs:1, 12 or 13.

14. The method of claim 11 wherein step (b) includes the step of hybridizing said amplified nucleic acid product with a signal primer comprising SEQ ID NOs:4, 5, 16 or 17.

15. The method of claim 12 wherein the SDA reaction comprises a thermophilic Strand Displacement Amplification (tSDA) reaction.

16. The method of claim 15 wherein the tSDA reaction is a homogeneous fluorescent real time tSDA reaction.

17. A method for amplifying a target nucleic acid sequence of SARS-CoV comprising: (a) hybridizing to the nucleic acid (i) a first amplification primer comprising the target binding sequence of SEQ ID NO:2; and (ii) a second amplification primer comprising the target binding sequence of SEQ ID NO:3; and (b) extending the hybridized first and second amplification primers on the target nucleic acid sequence whereby the target nucleic acid sequence is amplified.

18. The method of claim 17 wherein the first amplification primer comprises the target binding sequence of SEQ ID NO:15 and the second amplification primer comprises the target binding sequence of SEQ ID NO:16.

19. The method of claim 17 wherein the target binding sequences of SEQ ID NO:2 and SEQ ID NO:3 comprise a sequence required for an amplification reaction.

20. The method of claim 18 wherein the target binding sequences of SEQ ID NO:15 and SEQ ID NO:16 comprise a sequence required for an amplification reaction.

21. The method of claim 19 wherein the sequence required for the amplification reaction comprises a restriction endonuclease recognition site that is nickable by a restriction endonuclease.

22. The method of claim 19 wherein the sequence required for the amplification reaction comprises a promoter recognized by an RNA polymerase.

23. The method of claim 20 wherein the sequence required for the amplification reaction comprises a restriction endonuclease recognition site that is nickable by a restriction endonuclease.

24. The method of claim 20 wherein the sequence required for the amplification reaction comprises a promoter recognized by an RNA polymerase.

25. The method of claim 17 further comprising indirectly detecting the amplified target nucleic acid by hybridization to a signal primer.

26. The method of claim 25 wherein the signal primer comprises SEQ ID NO:4, 5, 16 or 17.

27. The method of claim 17 wherein the target nucleic acid comprises SEQ ID NOs:6, 7, 18 or 19.

* * * * *

SEQUENCE LISTING

<160> NUMBER OF SEQ ID NOS: 20

<210> SEQ ID NO 1
<211> LENGTH: 21
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 1
caacgctgag gtgtgtaggt g                                              21

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgattccgct ccagacttct cgggatacca cgtcgcaatg t                        41

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accgcatcga atgcatgtct cgggatgaag accagtaatg a                        41

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttagcca ccatacggat gtccagttac attttctgct tg                       42

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttagcca ccatacttga gtccagttac attttctgct tg                       42

<210> SEQ ID NO 6
<211> LENGTH: 118
<212> TYPE: DNA
<213> ORGANISM: Human Severe Acute Respitory Syndrome Coronavirus

<400> SEQUENCE: 6
ataccacgtc gcaatgtggc tacattacaa gcagaaaatg taactggact ttttaaggac    60
tgtagtaaga tcattactgg tcttcatcct acacaggcac ctacacacct cagcgttg     118

<210> SEQ ID NO 7
<211> LENGTH: 118
<212> TYPE: RNA
<213> ORGANISM: Human Severe Acute Respitory Syndrome Coronavirus -continued

<400> SEQUENCE: 7
auaccacguc gcaaugggc uacauuacaa gcagaaaaug uaacuggacu uuuuaaggac    60
uguaguaaga ucauuacugg ucuucauccu acacaggcac cuacacaccu cagcguug    118

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tcccgagtac gttagccacc atacggat    28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
acccgagtag ctatccgcca taagccat    28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tccccgagta cgttagccac catacttga    29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tccccgagta ctgatccgca ctaacgact    29

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atattatgcc agccacc    17

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atattatgcc agccaccgt                                                        19

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtaatccgc tccagacttc tcgggaatag acagtttcat cag                             43

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
accgcatcga atgcatgtct cgggttccaa ttaccacagt                                 40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgttagcca ccatacggat tgaagtcaat agccgccact                                 40

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttagcca ccatacttga ttgaagtcaa tagccgccac t                               41

<210> SEQ ID NO 18
<211> LENGTH: 101
<212> TYPE: DNA
<213> ORGANISM: Human Severe Acute Respitory Syndrome Coronavirus

<400> SEQUENCE: 18
aatagacagt tcatcagaa attattgaag tcaatagccg ccactagagg agctactgtg            60
gtaattggaa caagcaagtt ttacggtggc tggcataata t                              101

<210> SEQ ID NO 19
<211> LENGTH: 101
<212> TYPE: RNA
<213> ORGANISM: Human Severe Acute Respitory Syndrome Coronavirus

<400> SEQUENCE: 19
aauagacagu ucaucagaa auuauugaag ucaauagccg ccacuagagg agcuacugug            60

-continued

```
guaauuggaa caagcaaguu uuacgguggc uggcauaaua u                    101

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaaggaggga tgtgct                                                16
```